United States Patent [19]
Siclari et al.

[11] 4,085,127
[45] Apr. 18, 1978

[54] METHOD FOR PRODUCING ALDEHYDE ACIDS BY SELECTIVE OZONIZATION OF CYCLO-OLEFINS

[75] Inventors: Francesco Siclari, Barlassina; Pietro Paolo Rossi, Garlasco, both of Italy

[73] Assignee: SNIA Viscosa Societa' Nazionale Industria Application Viscosa S.p.A., Milan, Italy

[21] Appl. No.: 486,992

[22] Filed: Jul. 10, 1974

[30] Foreign Application Priority Data
Jul. 11, 1973  Italy .................. 26479A/73

[51] Int. Cl.² .............................. C11C 1/00
[52] U.S. Cl. ................... 260/413; 260/404; 260/405; 260/526 R
[58] Field of Search ............. 260/413, 404, 526 R, 260/405

[56] References Cited
U.S. PATENT DOCUMENTS 3,856,833   12/1974   Siclari et al. .............. 260/413
3,868,392   2/1975    Siclari et al. .............. 260/340.3

Primary Examiner—Winston A. Douglas
Assistant Examiner—John F. Niebling

[57] ABSTRACT

A mixture containing cyclo-olefin in concentrations of from 10 to 40% is subjected to a selective ozonation step to produce a heavy phase containing a mono-ozonide of the cyclo-olefin. The heavy phase is insoluble in the mixture and therefore settles and is drawn off and subjected to a transposition step to remove a single unsaturation, and produces an acidic aldehyde, which is thereafter subjected to an amination or hydrogenation process to produce unsaturated products having important applications as polymers or copolymers.

22 Claims, 11 Drawing Figures

OHC-CH$_2$-CH$_2$-CH=CH-CH$_2$-CH$_2$-COOH    T.Q. (NaCl)

Fig. 9

H$_2$N-CH$_2$-CH$_2$-CH$_2$-CH=CH-CH$_2$-CH$_2$-COOH    T.Q. (NaCl)

Fig. 9/A $H_2N-CH_2-CH_2-CH_2-CH=CH-CH_2-CH_2-COOH$ (NUJOL) (KBr)

Fig. 10

METHOD FOR PRODUCING ALDEHYDE ACIDS BY SELECTIVE OZONIZATION OF CYCLO-OLEFINS

BACKGROUND OF THE INVENTION a. Field of the Invention

This invention relates to a method for the production of unsaturated linear polyfunctional compounds, the concrete industrial importance of which will be indicated hereafter, and of their unsaturated and saturated derivatives, starting from poly-unsaturated cyclo-olefins, of which a satisfactory availability exists and the possibility of treatment and exploitation of which have been identified by the Applicant, as also hereinafter indicated.

This invention also has as its subject matter novel products having industrial importance as defined hereafter.

More specifically, the present invention concerns a method for the production, by means of processes including steps of ozonization and then of transposition of omega-formylalkenoic acids and their unsaturated derivatives starting from cyclododecatriene, cyclododecadiene, cyclooctadiene and cyclodecadecene (in the various forms and mixtures of stereoisomeric forms), and that is to say of open-chain unsaturated polyfunctional products having concrete possibilities of widespread and immediate industrial application and themselves forming subject-matter of the present invention. The unsaturated products, in particular, have important applications as polymers or as copolymers whose specific and potential reactivity, due to the presence of double bonds, enables them to find interesting uses for the manufacture of products which in turn possess particular properties, for example textile products possessing a high degree of dyeability, additives for anti-static agents or for resins and other products, all of which is easily understandable by persons skilled in the art.

As is known, cyclododecatriene-1,5,9, and likewise cyclodecadiene and cyclooctadiene, are products that are obtained by known process of cyclization of butadiene, are currently available on the market and are supplied by refineries and industries which treat and process petroliferous products. These cyclo-olefins are in general transformed by the petroleum processing industries themselves, or by the utilizer industry, into the corresponding cyclomonounsaturated product. For example, cyclododecene is obtained, which is for example notoriously utilized for the production of conventional nylon 12.

b. The Prior Art

The effective and concrete industrial utilization of starting materials which in any case entail more than one unsaturation, to obtain, with high conversions, acidic aldehydes and other open-chain unsaturated functional products (a utilization confirmed by the experimental work of the Applicants, which experimental work has demonstrated the importance and the concrete possibility of new industrial developments) is not known in the technical and patent literature of the art. Thus, at least within the limits of the Applicants' knowledge, it can be held that no known technology exists previously to the present invention.

It is in fact known that the mono-ozonization of poly-unsaturated olefins is a difficult operation, and that in practice it is performed only in the experimental field, with the obtaining of unacceptably low yields.

Generally, when an olefin has several double-bonds, the ozonization is not selective and more than one double bond becomes ozonized.

In the ozonization of cyclooctotetraene, i.e. of a cycloolefin having conjugated double bonds, for example (N. A. Milas — J. Org. Chem. 23 (1958/624)), followed by reduction with sodium disulphite, there is obtained approximately 2.2 millimoles of glyoxal (OHC-CHO) per millimole of cyclooctotetraene, which is a result that indicates that more than one double bond has reacted with the ozone.

By ozonizing in solution, either with polar solvents or with non-polar solvents or with mixtures of the same, the ozonization of more than one double bond is avoided when the double bonds are not equivalent or are sterically impeded or non-reactive with ozone (J. E. Franz. U.S. Pat. No. 3,481,954).

In some cases it proves possible to ozonize only one double-bond of a poly-unsaturated cycloolefin by using large excesses of cyclo-olefin and small amounts of ozone. In such cases, the process is clearly anti-economical since it is necessary to separate, with complicated means, small amounts of mono-ozonide from large amounts of cyclo-olefin.

In the previous publications of French patent applications No 72.05593 and No 72.05594 (corresponding to applicants' U.S. Pat. Nos. 3,856,833 and 3,868,392) there was fully described and exemplified a particular methodology for the continuous production of the ozonide of a cyclo-olefin without involvement of the well-known phenomen of superoxidation. The method is based on the principle of immediate separation of the hydroperoxide, which forms as the result of reaction of the ozonide with a reactive solvent, from the environment of ozonization, by means of the use of non-solvent for the hydroperoxide.

The present Applicants have now found that, in the case of poly-unsaturated cyclo-olefins, there is obtained a more rapid and instantaneous separation of the peroxide derivative of the ozonide if addition is made to the polar solvent, generally consisting of a carboxylic acid, an anhydride of an organic acid also. The polar solvent, the anhydride of the carboxylic acid, the non-polar solvent and the polyunsaturated olefin must be at least partially soluble one with another.

The ozonide of a poly-unsaturated cyclo-olefin represents an important intermediate for the preparation of unsaturated polyfunctional compounds. This conversion is effected with yields which exceed 90%, by means of re-arrangement of the ozonide at low temperature.

The reaction is catalyzed by the combination of the anhydride of a carboxylic acid and of the alkaline salt of a carboxylic acid. Both the low temperature and the catalytic system reported are essential for the purposes of obtaining from the ozonide of a cycloolefin a single derived product and not mixtures of products.

It is in fact known (U.S. Pat. No. 2,891,988 in the name of Brokmann) that by heating the ozonides, even in the presence of reducing agents and of water, there are obtained more or less complexed mixtures of different compounds, which, in particular, are difficult to separate.

Both the potential and concrete properties of the novel method characteristic of the present invention, which method in its broadest aspect is manifested in the treatment of a cycloolefinic starting product having more than one unsaturation, and in the formation of unsaturated intermediates and/or derivatives and/or end-products, in themselves forming subject matter of the invention and which are obtained always conserving at least one unsaturation, can be expressed initially by the following principal advantages:

— the starting unsaturated cycloolefins, such as cyclododecatriene and cyclooctadiene as available on the market, can be considered high-purity products. Even in the case of cyclododecatriene, which is in practice a mixture of its various stereoisomeric forms, the product cannot for such reason be considered impure, in view of the practically identical behaviour of these stereoisomeric forms in the subsequent treatments and conversions (ascertained by the Applicants), even though they lead to physico-chemical diversities in the unsaturated end-products, which fact in its turn represents an advantage in that it makes possible the selective obtaining of unsaturated compounds having different properties.

— in the case of production of unsaturated aminoacids, the said unsaturated end-products (in the case in point 12-aminododecadienoic -10-aminodecenoic and 8-amino-octenoic acids), when subjected to saturation processes, in particular hydrogenation, for the obtaining of the corresponding saturated aminoacids, always lead to saturated end-products having identical characteristics and properties, which are thus perfectly suitable for the subsequent processings or industrial productions foreseen.

These apprehensions, findings and the said experimental confirmation of the Applicants are, together, of great importance, particularly with respect to the aforementioned known art (which is currently held to be the only one with concrete industrial applications), according to which the product of cyclization of butadiene is first given treatments of selective or controlled hydrogenation to obtain its conversion into mono-unsaturated cycloolefin.

In fact, for example in the case of cyclododecatriene, in such conversion, in addition to cyclododecene (even though in prevalent quantity) there are also formed cyclododecane and cyclododecadiene. The said secondary fractions are among other things a cause of low industrial efficiency, in that they correspond to amounts which cannot be converted into the end products. The separation of these secondary fractions is generally intricate, costly, and sometimes incomplete. Moreover, it is known that these initial methods of conversion of the starting polyunsaturated cycloolefin, and that is to say the processes of selective hydrogenation, are, in their turn, extremely expensive. This initial selective hydrogenation, which is considered indispensable according to the present methods should in particular be compared with the method characteristic of this invention, when it is supplemented, as outlined above, by the conversion of the unsaturated aminoacid, specifically of the 12-aminododecadiene-oic acid, or the 12-aminododecenoic acid, or their admixtures, into the corresponding saturated aminoacid, inasmuch as the latter conversion does not require any special care or expedient.

SUMMARY OF THE INVENTION

Essentially, the method according to the invention is characterized by the fact that a cycloolefin with more than one unsaturation (in the case in point cyclododecatriene, cyclooctadiene and cyclodecadiene) is subjected to a step of selective ozonization from which is obtained the monoozonide of the said cycloolefin (with quantitative conversions and yields), which, in turn, is subjected to a transposition step leading to the obtaining of an acidic aldehyde, not more than one unsaturation being in any case removed in the said steps, the said acidic aldehyde being subsequently in its turn treated to obtain industrial products, part of which are novel in the art, themselves forming subject matter of the invention.

The principal products forming subject matter of the invention are unsaturated linear acids, in the specific instance containing from 8 to 12 carbon atoms. When obtained from cyclododecatriene, they correspond to the formula:

in which R is or —CH$_2$—NH$_2$.

Clearly, the compounds that are obtained from the polyunsaturated cycloolefins having 8 or 10 carbon atoms correspond to similar formulae, in which —R— remains as indicated whereas the residual acid indicated has 7 and 9 carbon atoms respectively.

More particularly, according to the invention, the starting polyunsaturated cycloolefin, particularly cyclododecatriene, cyclodecadiene and cyclooctadiene (independently, as has been said, of the form or mixture of isomeric forms and also, in the specific case of cyclododecatriene, possibly in admixture with cyclododecadiene) is treated by means of a sequence of steps and operations during which not more than one unsaturation is removed, the said sequence comprising a selective ozonization from which is obtained the monoozonide of the same starting product, such monoozonide being converted, by transposition, into unsaturated aldehyde acid such as the omega-formyl-alkenoic acids, in the case in point 11-formyl-4,8-undecadienoic acid (as well as 11-formyl-4-undecenoic acid or 11-formyl-8-undecenoic acid and their mixtures, 7-formyl-4-heptenoic acid, 9-formyl-4-nonenoic acid and 9-formyl-6-nonenoic acid which constitute intermediate products which are novel to the best of the applicants' knowledge and, as such, subject matter of the invention, and from which there can have origin a series of novel unsaturated products, readily obtainable, some of which of concrete and immediate industrial applicability and exploitability and others of which (the Applicants cannot at the present time affirm that they have discovered all the real possibilities of the present invention) of predictable future development, in view of the vastness of the technological field opened up by this invention.

In the course of the detailed description that follows, referred to various examples of execution of the invention, certain of these products and their possible uses are indicated. Particular interest attaches to the corresponding unsaturated aminoacids.

For example, from 12-aminododecadienoic acid there is obtained 12-aminododecanoic acid, notoriously utilizable for the production of nylon 12. Similarly, from 8-amino-octenoic acid and from 10-aminodecenoic acid there are obtained respectively 8-amino-octenoic acid and 10-aminodecanoic acid, which are utilizable for the production of nylon 8 and nylon 10 respectively. From the omega-aminoalkenoic acids there are obtained interesting unsaturated polyamides, which are characterized by comprising at least one double bond C=C in their recurring monomeric units.

From among the other novel unsaturated products that can be obtained according to the invention, the industrial importance of which is both foreseen and easily imaginable, there can be mentioned 12-hydroxy-4,8-dodecadienoic acid and 8-hydroxy-4-octenoic acid, from which there can be obtained unsaturated esters and/or polyesters, and, respectively, the methyl ester of the above-indicated acids, as well as a series of by-products, among which 1,12-diaminododecadiene (-4,8-) has been identified.

Over and above these, the method forming subject matter of the present invention provides, as by-products, the 1,12-dodeca -4,8-diene-diamine and 1,12-dodecandioic acid. From these, by polycondensation, there is obtained —unsaturated 12,12 nylon, or, by hydrogenation of the olefinic unsaturations and subsequent polycondensation, —saturated 12,12 nylon.

This novel methodology has proved possible as a result of the fact that out of the plurality of double bonds present in the starting polyunsaturated cycloolefin, in particular out of the two or three double bonds available, only one is eliminated in the said sequence of steps and operations (provided suitable expedients are adopted), which is not suggested by the prior art. This preservation of double bonds is the essential factor enabling the aforesaid products to be obtained and, foreseeably, also numerous other unsaturated products and derivatives which are also encompassed by the scope of the present invention, from the acidic aldehyde in its turn unsaturated. The fact that such sequence of steps generally comprises ozonization of cycloolefins and subsequent treatments directed towards the obtaining of acidic aldehydes (in the field of saturated products) and can be completed by processes of reductive amination does not alter the novelty or importance of the method according to the invention. These known methods and treatments have been only recently and to a limited extent divulged. As purely theoretical sources of the technique of reductive amination of saturated acidic aldehydes, mention can be made of the publication by H. Otsuki "Advances in Chemistry (Series 21-1959)". As regards the production of these saturated acidic aldehydes by means of ozonization of the corresponding cyclo-olefin, reference is made to the French patent applications No. 72.05593 and No. 72.05594 and to the above-noted corresponding U.S. Pat. Nos. 3,756,833 and 3,868,392, of the same applicants.

As demonstration of the feasibility of the present invention, there is hereafter set out a detailed disclosure of methods or procedures exemplifying ways of obtaining the novel products according to the invention. This disclosure is completed by the annexed drawings, in which:

FIGS. 3 to 10 reproduce a like number of IR and NMR spectra in respect of certain unsaturated compounds obtainable according to the invention, in particular:

Figure 5:
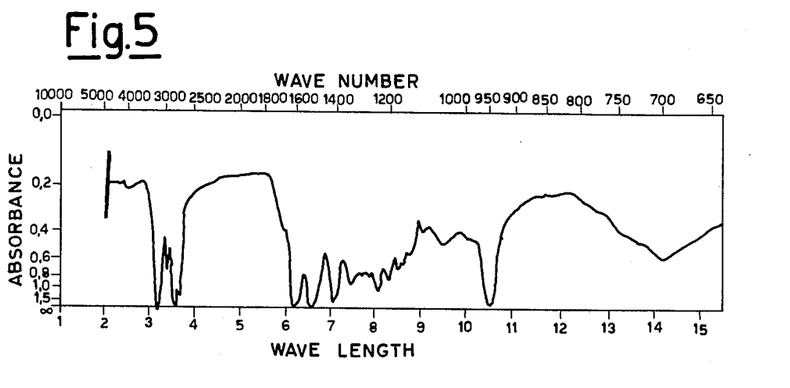
FIG. 5 gives the IR spectrum of the unsaturated polyamide as obtained from the said aminoacid.
Figure 6:
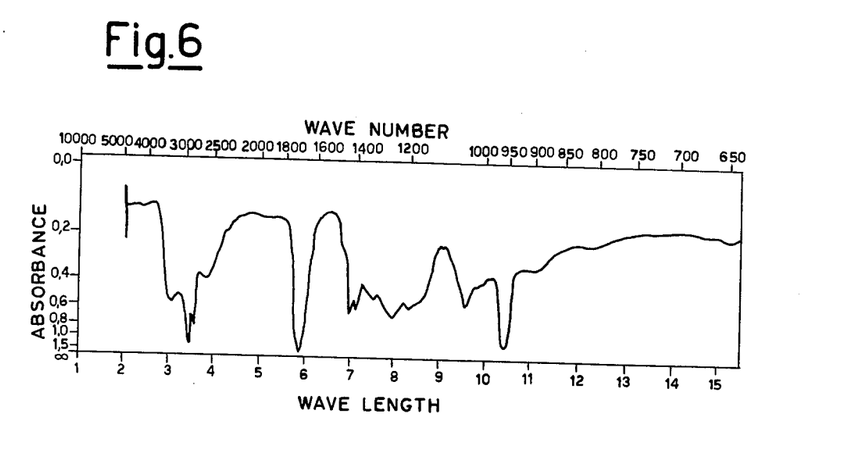
FIG. 6 gives the IR spectrum of the 12-hydroxy-t, t-4, 8-dodecadienoic acid obtainable from the unsaturated acidic aldehyde the spectrum of which is shown in FIG. 3.
Figure 7:
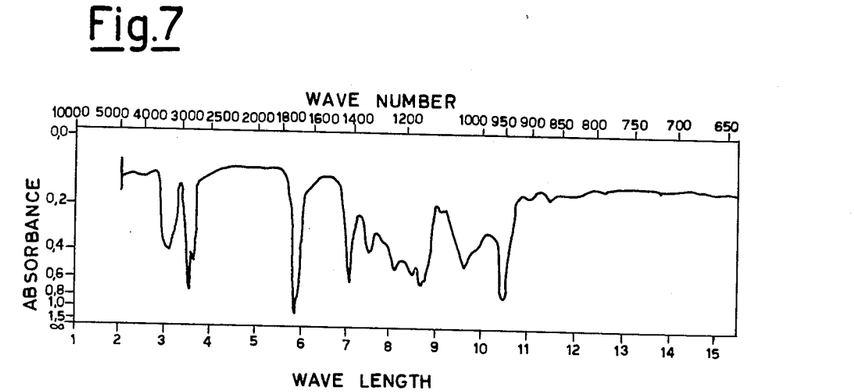
FIG. 7 gives the IR spectrum of the methyl ester of the said hydroxyacid.

Examination of these spectra clearly reveals the following: for the group represented by FIG. 3 to FIG. 7 the band of the trans double bond (960 cm$^-$) is preserved; the conversion both of 12 and 8 acidic aldehyde to unsaturated aminoacid leads to the disappearance of the band typical of the aldehydes (C—H at approximately 2700 cm$^{-1}$) and to the appearance of the bands characteristic of the NH$_3$ + (approximately 2200 cm$^{-1}$) of the aminoacids, while in FIG. 5 which represents the 12-unsaturated polyamide there no longer appears the NH$_3$+ band whereas there do appear the bands characteristic of the polyamides; in the 12-unsaturated hydroxyacid derivatives of FIG. 6 and methyl ester of FIG. 7 the band of the OH appears at approximately 3200 cm$^{-1}$.

Figure 8:
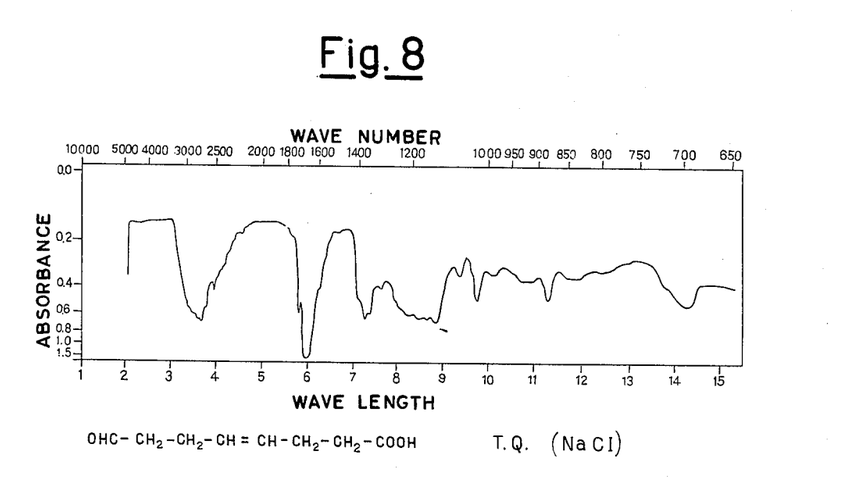
FIG. 8 shows the IR spectrum of 7-formyl-cis-4-heptenoic acid.
Figure 9:
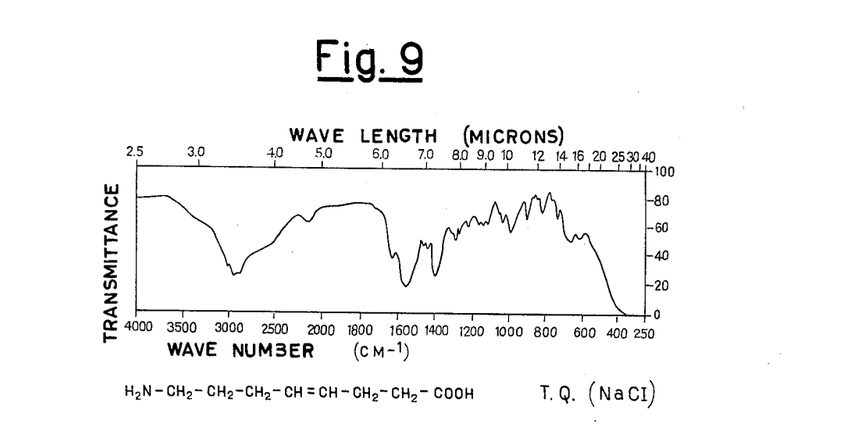
FIGS. 9 and 9/A give the IR spectra, obtained with two different methods, of 8-amino-cis-4-octenoic acid.

In the group from FIG. 8 to FIG. 9, which represents the 8-unsaturated acidic aldehyde and the corresponding 8-unsaturated aminoacid obtained from the cis, cis-1,5-cyclooctadiene, there is preserved the cis band between 680 and 740 cm$^{-1}$, while there are clearly visible the bands characteristic of the aldehyde group and of the protonic amino group of the aminoacids respectively (approximately 2200 cm$^{-1}$).

Figure 10:
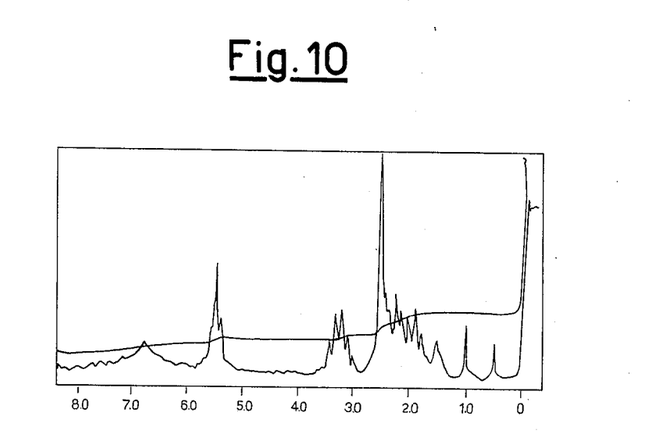
FIG. 10 shows the NMR spectrum of 8-amino-cis-4-octenoic acid.

In the NMR spectrum of the 8-amino-cis-4-octenoic acid dissolved in CF$_3$COOH there is confirmed the presence of the NH$_3$+ group (broadened peak centred at 3.23 $\tau$, integration = 3H) and of the cis double bond (peak centred at 4.53 $\tau$, integration = 2H).

In the ensuing description specific indication will be made of the stereoisomeric forms and relative mixtures utilized, in the interests of greater bearing on the industrial field, in view of the availability on the market of poly-unsaturated cycloolefins, in the case in point cyclododecatriene in various stereoisomeric forms, and also cyclodecadiene and cyclooctadiene.

In the IR spectra given in FIGS. from 3 to 7, on the other hand, there has been specified the utilization of 1,5,9-t, t, t-cyclododecatriene as starting product and this simply because the relative derivatives show clearly in the IR the trans isomerism of the double bond, without this in any way limiting the scope of the invention, while for the cyclooctadiene the novel product used was cis-cis-1,5-cyclo-octadiene.

The method characteristic of the invention will be described hereinafter summarily in its industrial applications directed towards the manufacture of 12-aminododecanoic acid, in its turn destined for the production of nylon 12 (which, although selected as example, is not restrictive inasmuch as the technology in question is applicable to nylons 8 and 10).

Clearly, the novel unsaturated products which are characteristic of the invention are in such cases merely in the form of intermediates for this complete process, there not moreover being excluded all other kinds of methods, or the use of different equipment, in the event of specific actuation of the invention for the obtaining of the said unsaturated products and of their derivatives.

Figure 1:
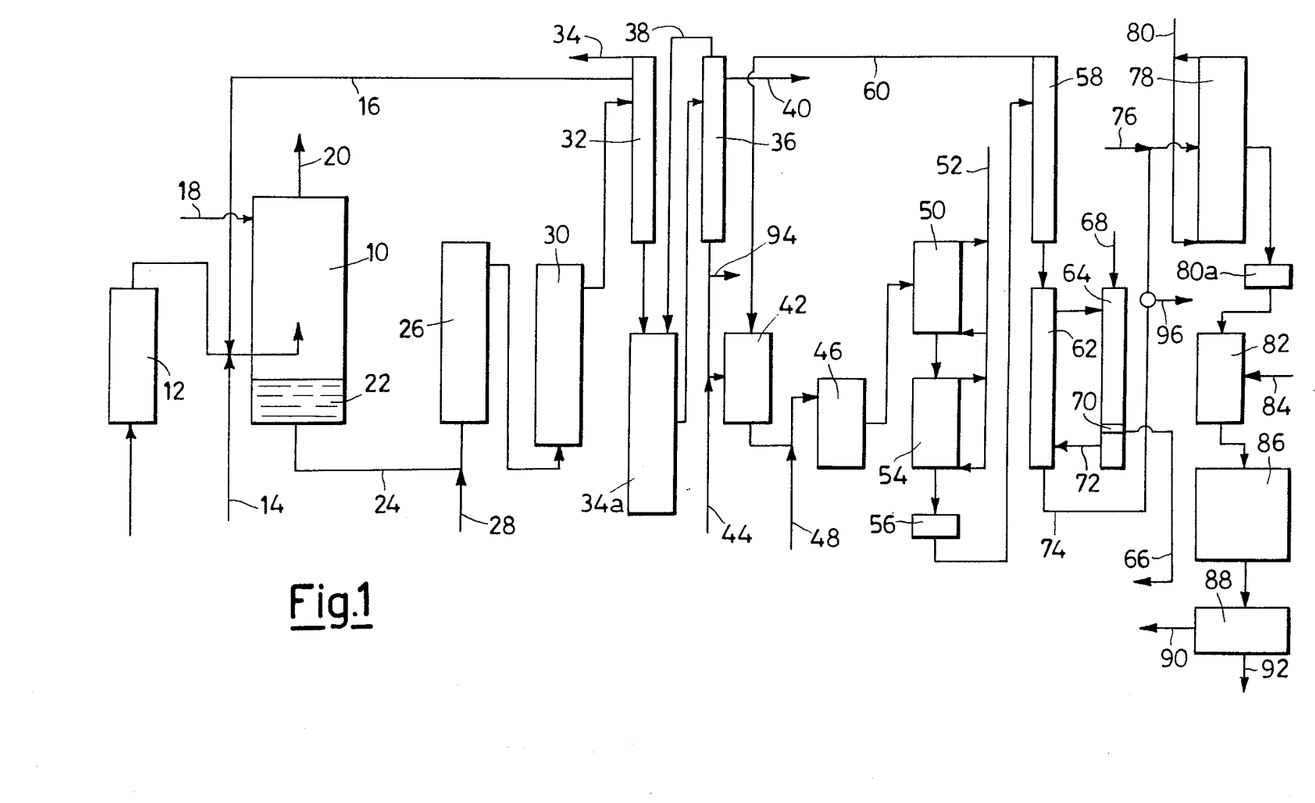
FIG. 1 shows schematically, in that the various components are individually well known, an installation utilizable for the preparation of 12-aminododecanoic acid from cyclododecatriene, that is to say of an important industrial product obtainable by the final treatment of the polyunsaturated aminoacid constituting what can at the present time be considered one of the principal products obtainable according to the invention.

The initial step of treatment of the polyunsaturated cycloolefin is carried out in the vessel or reaction environment indicated generally by 10, in association with an apparatus 12 for production of ozone, after prior preparation of a stationary phase consisting of a mixture of high-boiling saturated hydrocarbon, preferably from mineral oil (vaseline oil or refinery cuttings) with a polar solvent, such as acetic acid, and/or acetic anhydride, by using a mixture of $O_2 + O_3$ containing from 5 to 80 grams, and preferably from 15 to 60 grams of $O_3$ per cubic meter, or a mixture of $O_2 + O_3 + CO_2$ containing from 5 to 50 grams of ozone per cubic meter, or purified air plus ozone, stripped from nitrogen oxydes by having it passing in sodium acetate dissolved in acetic acid or caused to flow over CuO and containing from 1 to 50 grams of $O_3$ per cubic meter. The result is thus that the as-formed ozonide is continually deposited in the container bottom as a heavy phase P formed by a solution in acetic acid and/or acetic anhydride. This stage can be carried out at any temperature comprised between 5° C and 45° C. The acetic acid and/or acetic anhydride are fed in at 14 and also recycled at 16. Cyclododecatriene is fed in continually at 18, while at 20 the oxygen or other gas used as a vehicle for ozone is discharged.

This heavy phase, indicated at 22, is metered and sent at 24 into a transposition apparatus 26 wherein it is also metered at 28 an additional transposition catalyst, preferably sodium acetate, and possibly potassium acetate, sodium propionate and potassium propionate.

The transposition stage at 26 is carried out at a temperature ranging from 10° to 50° C, a solution of the unsaturated acidic aldehyde in acetic acid and/or acetic anhydride being obtained. Preferably, the transposition run is carried out in a sequential set of apparatus, by transferring the solution to a second apparatus 30 from which the product is passed to an evaporator 32. From the evaporator there is removed at 34 the excess acetic acid, whereas the acetic acid and/or acetic anhydride which are distilled off are recycled at 16 into the ozonization environment 10. The temperature in the two transposition stages (26-30) can either be constant or it can be increased, as a rule, from 26 to 30.

In the evaporator 32 the anhydride of the acidic aldehyde is left, which is converted into a hydrolysis apparatus 34a. The hydrolysis of the acidic aldehyde is carried out in such apparatus. Hydrolysis is effected with water at a temperature ranging from 50° C to 100° C. The solution is transferred to an evaporator 36, wherefrom the hydrolysis water is recycled at 38 into the hydrolizator 34a from which it is dumped, at 40, a mixture of the excess water and possibly acetic acid. From the bottom of the evaporator 36 the acidic aldehyde is discharged and transferred to an apparatus 42 for the formation of an imine (as exemplified hereinafter) which is fed at 44 with aqueous ammonia.

From the apparatus 42 the imine is withdrawn and transferred to an apparatus 46, fed at 48 with aqueous soda and Raney nickel, and where the conversion is effected of the ammonium salt into the imine of the acidic aldehyde into the sodium salt of the same imine, that is, by obtaining a compound in a form which is more favourable to the subsequent reductive amination treatment.

This solution is transferred to an autoclave 50 for hydrogenating the imine, wherein hydrogen is introduced at 52, under recycling conditions, said hydrogenation being completed in a second autoclave 54.

After having been passed through a filter 56 for removing the catalysts, the solution of the sodium salt of the unsaturated aminoacid is transferred to an evaporator 58 from which ammonia is distilled off (to be recycled at 60 into the imine formation apparatus 42), whereas the solution is transferred into an extractor 62 where the unsaturated diamine is extracted with toluene (or benzene or xylene or other appropriate solvents) and the light phase of this extraction is transferred to a separator 64 where the unsaturated diamine is precipitated from its solution in toluene as carbamate and removed at 66, the carbamate being obtained by reaction of the carbon dioxide, fed in at 68, with said unsaturated diamine. Through a filtering wall 70, the separation is effected of the carbamate, insoluble in toluene or other selected solvent, from the solvent which is recycled at 72 towards the extractor 62.

The aqueous solution of the sodium salt of the unsaturated amino acid, treated in the extractor 62 is sent, through a duct 74, and with the addition, at 76, of a hydrogenation catalyst (for example palladium) into a hydrogenation autoclave 78, fed at 80 with hydrogen, also under recycling conditions, the sodium salt of the saturated amino acid being thus obtained in aqueous solution.

The above indicated purification procedures as effected in the apparatus from 62 to 74 can be performed after the hydrogenation with palladium; in this case one obtains, as a by-product, the saturated diamine, in the form of the carbamate. From the carbamate the diamine is obtained by heating.

This solution of the sodium salt, withdrawn from the autoclave 78, is passed through the filter 80a for removing the catalyst, is transferred to a suitable container 82, to which carbon dioxide is fed in at 84, and the whole mass is transferred to another vessel 86 where crystallization and/or washing of the aminoacid take place, the latter being separated at 88 and discharged at 90, while the resultant mother liquors are removed at 92.

Obviously, if it is desired to use the unsaturated acidic aldehyde, characteristic of the invention, for other and different treatments and for obtaining the novel unsaturated compounds, which are also a characteristic of the invention, this acidic aldehyde, could be produced as described above and withdrawn, more particularly, at 94, downstream of the evaporator 36.

If one desires the unsaturated aminoacid, for example for the production of unsaturated polyamides, in the case in point unsaturated nylon-12, the latter can be withdrawn, in its turn, at 96, that is, downstream of the extractor 62.

Figure 2:
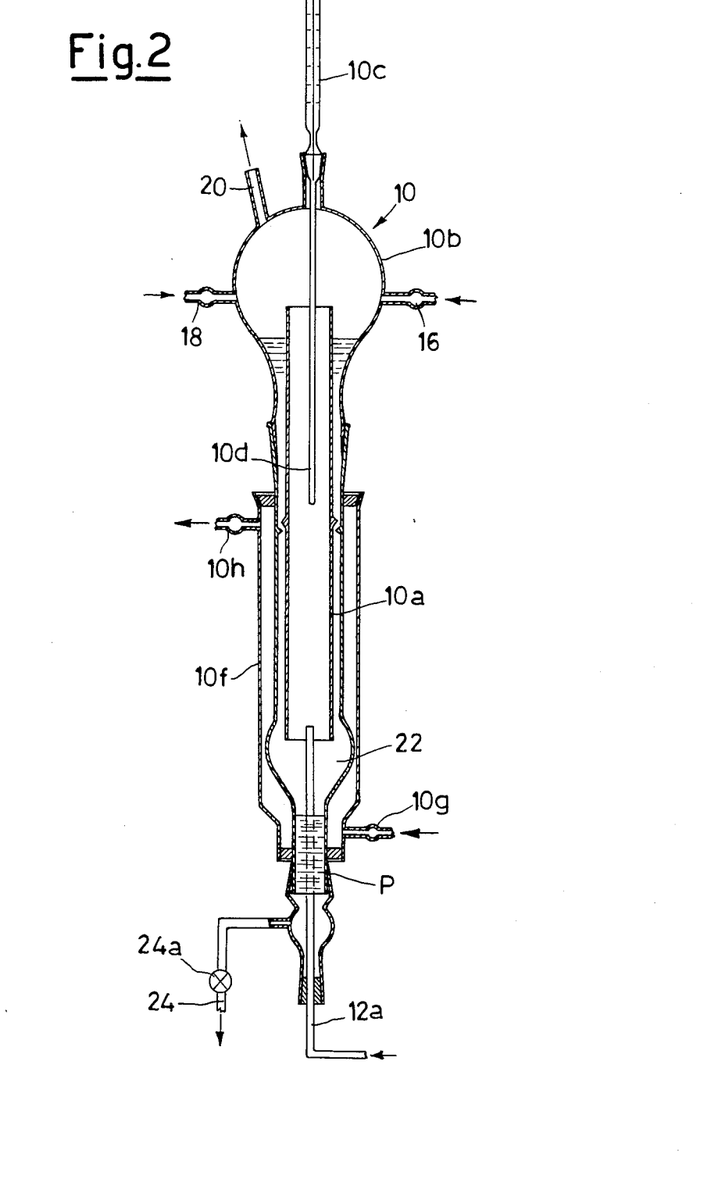
FIG. 2 shows in greater detail the equipment preferably used for the ozonization step.
Figure 3:
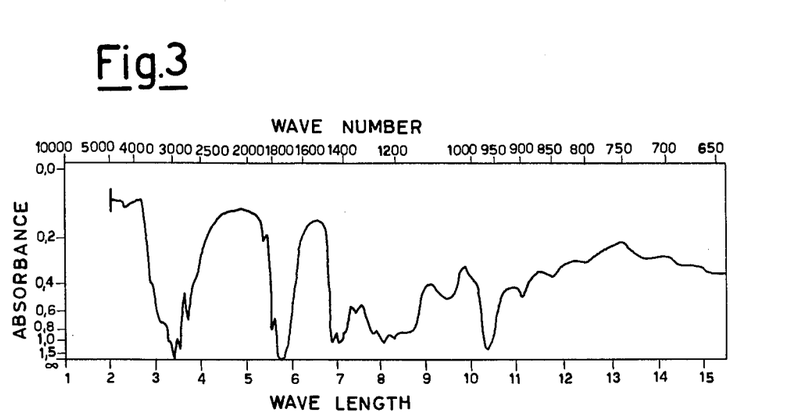
FIG. 3 gives the IR spectrum of 11-formyl-t, t-4, 8-undecadienoic acid.
Figure 4:
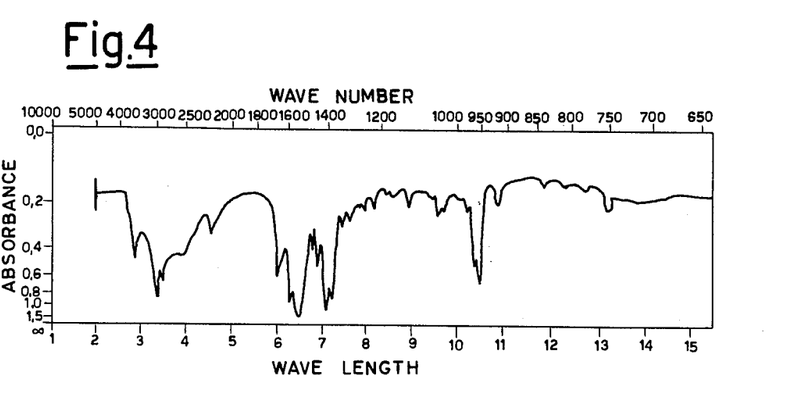
FIG. 4 gives the IR spectrum of 12-amino-t, t-4, 8-dodecadienoic acid obtainable by amination of the previous acid.

The ozonization apparatus 10 is reproduced in detail, in a preferred embodiment, and particularly selected for carrying out the invention, in FIG. 2 where the reference numerals as previously indicated connote component parts and equivalent members such as those shown diagrammatically in FIG. 1.

This apparatus substantially comprises an internal reaction tube 10a, whose top end enters a flask 10b in which pen the outlet 20 for the oxygen, and the ducts 18 for feeding in cyclododecatriene and 16 for feeding in the recycled acetic acid and/or anhydride. At 12a there is indicated the arrival duct, at the base of the reaction environment, of the product of the apparatus 12 for the production of ozone ($O_2 + O_3$) and at 24 there is indicated the discharge duct for the ozonide, as equipped with a suitable valve 24a.

The apparatus is completed by an appropriate thermometer 10c whose sensitive bulb 10d is extended into the reaction tube. The reaction portion proper for the collection of the ozonide is cooled by a jacket formed by an outer container 10f, integral with the inlet fitting 10g and the outlet fitting 10h for an appropriate coolant mixture.

Those which follows are specific examples relating to a few parameters and a few technological conditions which are deemed more suitable for the work, with high yields and under the novel and particular methods as developed on the basis of complementary considerations and field tests of the invention.

EXAMPLES — GROUP I (OZONIZATION)

I-1 OZONIZATION OF t, t, t-1,5,9-cyclododecatriene (CDT) in ACETIC ACID-ACETIC ANHYDRIDE — PARAFFIN OIL In this example there is described the preparation of the CDT mono-ozonide by ozonization in three solvents, formed by acetic acid, acetic anhydride, and paraffin oil.

The CDT mono-ozonide can be employed to obtain unsaturated aldehyde acids, saturated and unsaturated dicarboxylic acids or olialdehydes, which are useful products in themselves or for subsequent conversions.

In the vessel 10 of FIG. 1 there is charged 800 grams of t,t,t-1,5,9-cyclododecatriene (m.p. = 30°-32° C), purity 97.5%, 297 grams acetic acid, 503 grams acetic anhydride (purity 95.2%) and 6400 grams of paraffin oil. The temperature of the mixture is brought to 20° C and continual feeding is made of 113.5 grams/hour of ozone in 1700 liters/hour of oxygen (at ambient pressures), 736 grams/hour of acetic anhydride, 585 grams/hour of acetic acid, 400 grams/hour of CDT and 80 grams/hour of paraffin oil.

A heavy phase is continuously deposited on the bottom of the reactor, the said phase consisting of CDT mono-ozonide dissolved in the acetic anhydride - acetic acid mixture at the rate of 1900 grams/hour.

After 16 working hours, 30410 grams of ozonide solution has been continually discharged from the bottom of the reactor and sent to the transposition apparatus (No. 26, FIG. 1). The content of active oxygen (from iodometric assay according to Lohaus) was 37 mols overall, corresponding to 7760 grams of CDT ozonide as expressed in its classical form, the remainder being acetic anydride, acetic acid and small quantities of cyclododecatriene and paraffin oil.

The total reacted cyclododecatriene (calculated from the amount charged, from what is left in the reactor and what is contained in the heavy phase) was 37.5 mols, a result which, as a rough estimate, indicates that CDT has reacted with ozone in a ratio of 1 : 1.

These data show that it is possible quantitatively to convert a polyunsaturated cyclo-olefin into its mono-ozonide. By employing paraffin oil, hydrocarbon losses in the reaction gas are prevented.

I-2 OZONIZATION OF t,t,t-CDT IN ACETIC ACID — ACETIC ANHYDRIDE — CYCLOHEXANE

In this example, paraffin oil is replaced by cyclohexane.

The Example I-1 was repeated employing cyclohexane in lieu of paraffin oil, and, in this case, too, a 1 : 1 reaction of CDT in ozone was obtained, although some cyclohexane was removed by the reaction gas and it was thus necessary to reintegrate it in the ozonizer.

I-2-bis OZONIZATION OF cis,cis-1,5-cyclooctadiene

The Example I-2 is repeated, using cyclooctadiene (COD) as polyunsaturated cycloolefin.

From the relative quantities of cycloolefin and ozone reacted it can be seen that, in this case also, the ozone reacts to an extent of 1:1 in mols with the COD. The ozonide of the COD is a product useful for obtaining unsaturated aldehyde acid, bicarboxylic acids, etc.

I-2-tris OZONIZATION OF cis, trans-1,5-cyclodecadiene

The example No. I-2 is repeated (using cyclodecadiene (CDD) as cycloolefin). In this case as well, a 1 : 1 reaction between olefin and ozone is found.

The ozonide of CDD is an important product in that, besides having uses analogous to those recalled in respect of the ozonides of CDT and COD, it can serve as intermediate for the preparation of sebacic acid which plays a part in the field of plastics, additives, finishings for synthetic fibres.

I-3 OZONIZATION OF t,t,t-CDT IN ACETIC ACID-ACETIC ANHYDRIDE-CYCLOHEXANE BY EMPLOYING A MIXTURE OF OXYGEN, OZONE AND CARBON DIOXIDE

For the ozonization reaction pure ozone-laden oxygen can be used, or, on account of the hazards due to pure oxygen, there can be used a mixture of oxygen, carbon dioxide and ozone, in which the ratio of the three components of the gas mixture can be varied within a wide range. It is also possible to use air or ozone; in the latter case, however, the mixture of air and ozone contains nitrogen oxides which as nitrogenous acids tend to cause the polymerization of the ozonide as formed in the ozonization and thus do not permit to use this mixture in the industrial ozonizations. The applicants have found that by passing ozone-laden air on chips of copper oxide or through a solution of sodium acetate in glacial acetic acid, a gaseous mixture is obtained which is deprived of those nitrogen oxides which could originate nitrogenous acids.

Example I-2 has been repeated by employing as the ozonizing gas, instead of the mixture ozone and oxygen, a mixture of ozone-oxygen-carbon dioxide formed by 2.5% ozone, 57.5% oxygen and 40% of carbon dioxide, by volume. Also in this case there is obtained the CDT mono-ozonide with a yield of 95%.

I-4 OZONIZATION OF cis, t,t-CDT; cis,cis,t-CDT AND t,t,t-CDT IN ACETIC ACID, ACETIC ANHYDRIDE, PARAFFIN OIL The Example I-1 was repeated, using a mixture of the various stereoisomers of CDT (70% of cis,t,t-CDT; 27% of t,t,t-CDT; 2% of cis,cis,t-CDT and 1% of cyclododecane). The ozonizing gas consisted of a mixture of oxygen, ozone/carbon dioxide as in the Example I-3.

From the ozonization there was exclusively obtained the mono-ozonide of CDT.

I-5 OZONIZATION OF t,t,t-CDT WITH AIR AND OZONE STRIPPED FROM NITROGEN OXIDES BY COPPER OXIDE

Example I-1 has been repeated by employing a mixture of ozone-laden air which has been previously passed over copper oxide chips. The as obtained ozonide was not polymerized and was formed by the CDT mono-ozonide as in the example I-1.

I-6 OZONIZATION OF t,t,t-CDT WITH OZONE-LADEN AIR STRIPPED OF THE NITROGEN OXIDES BY PASSING IT OVER AN ACETIC ACID SOLUTION OF SODIUM ACETATE

Example I-1 has been repeated. The ozone-laden air has been passed through a 2% sodium acetate solution in glacial acetic acid. The gas emerges from the absorber virtually deprived of nitrogen oxides while the ozone contents does not undergo any decrease. With this mixture there has been ozonized the cyclododecatriene and the results have been equal to those of example I-1.

I-7 OZONIZATION OF CYCLODODECADIENE

Cyclododecadiene has been used as the polyunsaturated olefin, by repeating the ozonization as described at I-1. The as separated ozonide was formed by 95% by the mono-ozonide of cyclododecadiene.

EXAMPLES : GROUP II (TRANSPOSITION)

II-1 TRANSPOSITION OF THE MONO-OZONIDE OF t,t,t-CDT INTO 11-FORMYL-t,t-4,8-UNDECADIENOIC ACID

The transposition of the CDT mono-ozonide into 11-formyl-t,t-4,8 undecadienoic acid is carried out catalytically as described in the examples that follow. The 11-formylundecanoic acid and the aldehyde acids of the analogous series (having 8 and 10 carbon atoms) are important intermediates for their conversion into aminoacids, hydroxyacids, esters, for example for resins, etc.

The ozonide solution (1900 grams/hour) coming from the apparatus 10 of FIG. 1, is sent continuously onto the bottom of a first transposition apparatus (26, FIG. 1) consisting of a 6-compartment steel cylinder fitted with thermometer, turbine type stirrer and temperature-regulation jacket kept at 20° C. The transposition apparatus is also continuously fed with 4.75 grams/hour of sodium acetate dissolved in 42.8 grams of acetic acid. The mixture issuing from the top of the first transposition apparatus passes to a second transposition apparatus (30, FIG. 1) which is the same as the first and is temperature-regulated at 30° C. Both the transposition apparatuses are kept under an inert gas atmosphere (carbon dioxide). The overall stay time is 7 hours and 30 minutes. Stirring is very slow.

Taking as equal to 100 the percentage of active oxygen (peroxidic oxygen) at the inlet of the first transposition apparatus, the analysis of this latter variable at the outlet of the first transposition apparatus was 31.7% and at the outlet of the second transposition apparatus was 7.6% (conversion 92.4%). The solution coming out of the second transposition apparatus is sent to a liquid-film evaporator (32, FIG. 1) to remove the solvents. The residue, 526 grams/hour, of a liquid oily at room temperature, is continuously trated at 72° C with 526 grams/hour of water (stay time 60 minutes) in an inert gas (nitrogen) atmosphere (34, FIG. 1). The water is again evaporated as a liquid film (36, FIG. 1). There is obtained 539 grams/hour of an oily residue which still contains small amounts of water, acetic acid and paraffin oil; it has the following characteristics:

| | |
|---|---|
| Aldehydic groups | 4.2 millimols/gram |
| Acidic groups | 4.5 millimols/gram |
| double bonds | 8.8 millimols/gram |

The product boils at 180°–183° C at 3 mm. of residual pressure, and consists of 11-formyl-t,t-4,8-undecadienoic acid.

II-1-bis TRANSPOSITION OF THE OZONIDE OF CYCLOOCTADIENE

The example NO.II-1 is repeated, using the product obtained in the example 1-2-bis, and that is to say the mono-ozonide of cyclooctadiene (COD) is subjected to transposition.

There is obtained 7-formyl-4-heptenoic acid, which on analysis shows the following characteristics:
b.p. at 2.3 mm.Hg. = 146.5° C $\eta_D^{20}$ = 1.4744

| | calculated | found |
|---|---|---|
| double bonds (mmols from $H_2$/g. | 6.4 | 6.5. |
| —CHO-groups (titration with $H_2NOH \cdot HCl$ | 6.4 | 6.3 |
| —COOH groups (titration with NaOH) | 6.4 | 6.6 |

II-1-tris TRANSPOSITION OF THE OZONIDE OF CYCLODECADIENE

The example No.II-1 is repeated, using the product obtained in the Example I-2-tris, and that is to say transposing the mono-ozonide of cyclodecadiene (CDD). There is obtained a mixture of the 9-formyl-nonenoic acids, and that is to say of 9-formyl-4-nonenoic acid and 9-formyl-6-nonenoic acid.

II-2 TRANSPOSITION OF THE CDT MONO-OZONIDE OBTAINED FROM THE OZONIZATION OF MIXTURES OF cis,t,t-CDT; cis,cis,t-CDT AND t,t,t-CDT TO 11-FORMYL-4,8-UNDECADIENOIC ACID The product as obtained in Example I-4 is subjected to transposition as described in Example II-1. An oily compound is obtained, which is constituted by a mixture of the steric isomers of the 11-formyl-4,8-undecadienoic acid in an amount of grams/hour 528.

The product has a boiling point of 178°–185° C under 3 mms of mercury.

II-3 TRANSPOSITION OF THE MONO-OZONIDE OF t,t,t-CDT IN ACETIC ANHYDRIDE-POTASSIUM ACETATE 1900 grams/hour of a solution of the mono-ozonide of CDT (see Example I-1) have continually been sent to the bottom of a first transposition apparatus together with 5.5 grams/hour of potassium acetate dissolved in 45 grams of glacial acetic acid. The temperature of the transposition has been maintained at 25° C while a temperature of 35° C has been maintained in the second transposition apparatus.

By adopting the procedure set forth in Example II-1 there have been obtained 545 grams/hour of 11-formyl-t,t,-4,8-undecadienoic acid, impure due to small amounts of CDT-paraffin oil-acetic acid and water.

II-4 TRANSPOSITION OF THE MONO-OZONIDE OF CDT INTO PIRIDINE

The procedure set forth in II-3 has been adopted by using piridine-acetic anhydride as the transposition agents. At 30° C (first transposition apparatus) and at 45° C (second transposition apparatus) a 96% conversion of the active oxygen has been obtained.

II-5 TRANSPOSITION OF THE MONO-OZONIDE OF CYCLODODECADIENE INTO 11-FORMYL-4-UNDECENOIC ACID AND 11-FORMYL-8-UNDECENOIC ACID

Example II-1 has been repeated by effecting the transposition on the mono-ozonide of cyclododecadiene prepared according to Example I-7. There have been obtained, in total, 515 grams/hour of 11-formyl-4-undecenoic acid and 11 formyl-8-undecenoic acid.

In the Examples of the preceding groups there has been shown the advantageous production of unsaturated acidic aldehyde. Further examples now follow which relate to several possibilities of subsequent treatments of said acidic aldehyde to obtain several unsaturated products (characteristic of the invention) and also saturated compounds having a well known commercial importance.

EXAMPLES: GROUPS III (PRODUCTION OF UNSATURATED AMINO ACIDS AND RELATIVE UNSATURATED NYLONS)

III-1 REDUCTIVE AMINATION OF THE TRANSPOSITION PRODUCT OF THE OZONIDE OF t,t,t,-CDT INTO 12-AMINO-t,t,4,8-DODECADIENOIC ACID (BY-PRODUCT: 1,12-DIAMINO-DODECADIENE-(4,8) AND ITS CARBAMATE)

In this set of examples the possibility is shown of obtaining unsaturated amino acids from CDT. The amino acids are important intermediates to obtain unsaturated nylons. There is also obtained as a by-product the unsaturated diamine which can easily be separated from the alkaline solution of the aminoacid by extraction with a solvent of the kind benzene, toluene, chloroform, and others.

From the solution of the diamine in said solvents, the diamine is recovered as carbamate by treatment with carbon dioxide. From the carbamate the diamine is obtained by heating.

The unsaturated amino acid is obtained from its alkaline aqueous solutions by treatment with a weak acid, generally carbonic acid.

539 grams/hour of the transposition product of the CDT ozonide as obtained in Example II-1 are continually sent to a vessel for the preparation of the ammonium salt of the imine of the unsaturated acidic aldehyde (42, FIG. 1), together with 2420 grams/hour of an aqueous solution of ammonia (28% $NH_3$). The temperature is maintained at 15°-20° C by cooling; the stay time is 1 hour. The solution issuing from the apparatus for preparing the ammonium salt of the acidic aldehyde imine enters a second apparatus (46, FIG. 1) in which there are added 100 grams/hour of sodium hydroxide dissolved in 675 cu.cms water, which contains in suspension 33 grams of Raney nickel.

In this apparatus, by addition of sodium hydroxide there is completed the conversion of the ammonium salt of the imine of the unsaturated acidic aldehyde into the sodium salt thereof.

The catalyst is maintained in suspension by vigorous stirring. This suspension is continually sent to a first autoclave, (50, FIG. 1) maintained at a temperature of 95° C and at a pressure of 30 atmospheres with hydrogen. The reaction time is 30 minutes.

The suspension emerging from the first autoclave enters a second autoclave (for completing the reaction) at 95° C and 30 atmospheres (54, FIG. 1). The product issuing from the second autoclave is passed through a filter (56, FIG. 1) where the catalyst is collected and then into an evaporator under ambient pressure (58, FIG. 1) where the excess ammonia is stripped. The remaining solution is extracted continually with toluene at 90°-95° C (FIG. 1, Nos. 62 and 64).

The toluene extract is treated with $CO_2$ and the precipitate is collected by filtration at 70, FIG. 1. There are obtained 14 grams/hour of 1,12-diaminododecadiene-(4,8)-carbamate. Melting point 123.5°–128.5° C (decomposition).

| | Calculated millimols/gram ($C_{13}H_{24}O_2N_2$) | Found millimols/gram |
|---|---|---|
| Amino groups | 8.34 | 8.37 |
| Double bonds | 8.34 | 8.20 |

By heating the diamine carbamate in toluene, one obtains the unsaturated diamine b.p.$_3$ = 130° C. The aqueous phase is treated with carbon dioxide at zero ° C. A precipitate is obtained of 230 grams/hour of unsaturated amino acid. The mother liquors are treated with ethanol, the sodium bicarbonate, which precipitates, is collected on a filter and the filtrate is concentrated in vacuo and treated at 0° C again with carbon dioxide. There are obtained 115 additional grams/hour of a precipitate which is combined with the one precipitated at the outset. The combined precipitates are crystallized from water and there is obtained 298 grams/hour of unsaturated amino acid with m.p. of 190°–192° C (12-amino-t,t-4,8-dodecadienoic acid).

| | Calculated (mmols/gram) | Found mmols/gram |
|---|---|---|
| Total nitrogen | 4.74 | 4.67 |
| Primary aminic nitrogen | 4.74 | 4.69 |
| Double bonds | 9.48 | 9.37 |
| COOH groups | 4.74 | 4.78 |

The separation of the unsaturated amino acid from the aqueous solutions coming from the reductive amination is not complete.

III-1-bis REDUCTIVE AMINATION OF 7-FORMYL-4-HEPTENOIC ACID TO 8-AMINO-4-OCTENOIC ACID The example No. III-1 is repeated, using the unsaturated acidic aldehyde obtained in the example II-1-bis, preparing the barium salt of the imine of the acidic aldehyde, instead of the sodium salt, so as to be able to separate, after amination, the barium as sulfate and leave the amino acid in aqueous solution, from which separation is performed by evaporation of the water.

After crystallization by means of propyl alcohol/ethyl acetate (60/40), there is obtained 8-amino-4-octenoic acid, m.p. 139°-144° C.

| Analysis | Calculated | Found |
|---|---|---|
| Primary amino groups (Van Slyke) | 6.36 | 6.4 |
| COOH groups (meq./NaOH/gram) | 6.36 | 6.4 |
| Double bonds (mmols $H_2$/g.) | 6.36 | 6.3 |

III-1-tris REDUCTIVE AMINATION OF 9-FORMYL NONENOIC ACIDS

Operation is carried out as described in the Example III-1-bis, but using the unsaturated acidic aldehyde of the Example II-1-tris; thereafter operating as described in the Example III-1, there is obtained a mixture of 10-amino-4-decenoic and 10-amino-6-decenoic acids.

III-2 REDUCTIVE AMINATION OF THE TRANSPOSITION PRODUCT OF THE OZONIDE OF t,t,t,-CDT TO 12-AMINO-t,t-4,8-DODECADIENOIC ACID BY EMPLOYING AS THE CATALYST NICKEL AS OBTAINED BY DECOMPOSITION OF THE NICKEL FORMATE IN BOILING CYCLODODECANE

The purpose of this example is that of carrying out the reductive amination with a catalyst other than Raney nickel.

The procedure is the same as in example III-1. The nickel is obtained by suspending the nickel formate in cyclododec-ane and slowly heating the suspension up to 230°-235° C.

This temperature is maintained until the evolution of decomposition gas is over.

By employing this catalyst there are obtained 305 grams/hour of an unsaturated amino acid (m.p. 189°-192° C). The catalyst as obtained by decomposing the nickel formate in cyclododecane has an activity which is equal to that of the Raney nickel.

III-3 REDUCTIVE AMINATION OF THE TRANSPOSITION PRODUCTS OF THE OZONIDE OF cis,t,t-CDT AND cis,cis,t-CDT AND t,t,t-CDT TO UNSATURATED AMINO ACID The procedure is as in III-1. There are obtained 285 grams/hour of mixtures of isomers of the 12-amino-4,8-dodecadienoic acid.

III-4 REDUCTIVE AMINATION OF THE TRANSPOSITION PRODUCT OF CYCLODODECADIENE OZONIDE 11-formyl-4-undecenoic acid and 11-formyl-8-undecenoic acid are subjected to reductive amination as in III-1. There are obtained 420 grams/hour of monounsaturated amino acid with a m.p. of 186° C.

The procedure of reductive amination according to the Examples from III-1 to III-4 can be applied also to the saturated acidic aldehydes as is hereafter exemplified. In such case the separation of the amino acid, after the extraction of the saturated diamine, is performed by acidifying the alkaline salt or alkali-earthy salt of the amino acid by means of a weak acid (carbonic acid) or by means of a strong acid (sulfuric acid) and separating the amino acid either by means of crystallization or by evaporation of the aqueous solvent.

The preparation of the saturated acidic aldehyde from the unsaturated acidic aldehydes is described in the series of Examples from III-4-Bis/1 to III-4-Bis/3.

EXAMPLE III-4-Bis/1 — (Saturated acidic aldehyde from unsaturated acidic aldehyde at 20° C)

Two hundred grams of 11-formyl-4,8-undecadienoic acid consisting of a mixture of the trans, trans and cis, trans isomers, having boiling range of 179°-182° C at 3 mm.Hg. (purity 90% — Analysis : Aldehydic groups = 4.3 mmols/gram; acidic groups = 4.4 mmols/gram; double bonds = 8.6 mmols/gram, is dissolved in 466 grams of 98% acetic acid and charged into a steel autoclave, volume 1270 cu.cm. equipped with magnetic stirrer and with a temperature-regulation system made up of a jacket within which temperature-controlled water flows.

The autoclave is washed with nitrogen under nitrogen 8 grams of 5% Pd on carbon are charged. Then washing with hydrogen is carried out and 20 atmospheres of $H_2$ are charged.

The heat-regulation water is brought to 15° C and caused to circulate in the jacket of the autoclave. When the liquid inside the autoclave has reached a temperature of 15° C, stirring is commenced. The pressure drops rapidly and, when it is at 10 Atm., charge again at 20 atmospheres.

The reaction temperature rises from 15° to 20° C and then remains steady at this value. In a total of 20 minutes there were charged 52 atmospheres of hydrogen and, after this time, the absorption of hydrogen proves practically complete.

The autoclave is decompressed, placed under nitrogen and the solution is discharged through a filter. The filtrate is evaporated to dryness under vacuum.

There is obtained 196 grams of a waxy white solid residue with m.p. 62°-64° C and consisting of 11-formyl-undecanoic acid. (Analysis : CHO Group = 4.28 millemols — COOH Groups = 4.5 millemols/gram; double bonds = traces).

EXAMPLE No. III-4-bis/2 (Saturated acidic aldehyde from unsaturated acidic aldehyde at 40° C)

Into the autoclave utilized in the Example III-4-bis/1 there are charged 232 grams of 11-formyl-4,8-undecadienoic acid equal to that utilized in the Example No. 1, dissolved in 542 grams of 90% acetic acid (the remainder consisting of water). The procedure is as in the Example 1, causing to circulate in the jacket of the autoclave temperature-regulated water (35° C). Into the autoclave there are placed 10 grams of 5% Pd on carbon at 20 atmospheres of hydrogen. When the temperature inside the autoclave is at 32° C, the stirring is started and, when the pressure falls to 10 atmospheres, is brought back to 20 atmospheres. During the tests, the temperature — by effect of the heat of the reaction — goes to 40° C. After 36 minutes the absorption of hydrogen tends to cease. After a further five minutes the autoclave is decompressed, the catalyst is filtered and the acetic solution is evaporated under vacuum.

There is obtained 225 grams of 11-formyl-undecanoic acid, m.p. 61°–64° C.

EXAMPLE No. III-4-bis/3 (7-formyl-heptanoic acid from 7-formyl-heptenoic acid)

86 grams of 7-formyl-4-heptenoic acid (characteristics: boiling point 146.5° C at 2.3 mm Hg $\eta_D^{20} = 1.4744$; aldehydic groups = 6.35 mmols/gram; acidic groups = 6.6 mmols/gram; double bonds = 6.52 mmols/gram) are dissolved in 300 grams of glacial acetic acid, and placed into the steel autoclave described in the Example III-4-Bis/1. The autoclave is washed with nitrogen, 2 grams of 5% Pd on carbon are charged and placed under a pressure of 15 atmospheres with hydrogen.

The temperature of the temperature-regulating liquid goes to 15° C and, when the internal temperature is 15° C, the stirring is commenced, maintaining a constant pressure of 15 atmospheres.

After 20 minutes the absorption of hydrogen ceases. The solution is discharged, filtered from the catalyst and the solvent is evaporated under vacuum.

There is obtained 86.5 grams of 7-formyl-heptanoic acid with b.p.$_{0.1}$ = 130°–132° C.

By applying the procedure described to the 9-formyl-4-nonenoic acid there is obtained the 9-formyl-4-nonanoic acid.

III-5 POLYCONDENSATION OF THE 12-AMINO-t,t-4,8-DODECADIENOIC ACID 20 grams of unsaturated amino acid with m.p. 190°–192° C polycondensed at 210° C for 6 hours in an atmosphere of pure nitrogen.

There is obtained 18.2 grams of a polymer having a glossy ivory white color. Analysis on polymer : double bonds (catalytic hydrogenation in hexamethylphosphoramide = 9.2 millimols/gram); m.p. (DSC) = 189° C. Intrinsic viscosity (m-cresol) = 1.2.

EXAMPLES : GROUP IV (HYDROGENATION OF THE UNSATURATED AMINO ACIDS TO SATURATED AMINO ACID AND RELATIVE NYLON

IV-1 PREPARATION OF THE 12-AMINODODECANOIC ACID FROM 12-AMINO-t,t-4,8-DODECADIENOIC ACID

The saturated aminoacid, which represents the base product for the synthesis of the traditional nylons, is prepared by carrying out a catalytic hydrogenation on palladium on the solution of the unsaturated aminoacid. The separation of the product is similar to that reported under III-1.

The procedure is as in III-1 and preceding examples as regards the preparation of the unsaturated acidic aldehyde and the unsaturated aminoacid.

In the aqueous solution of the sodium salt of the 12-amino-t,t-4,8 dodecadienoic acid coming from the extraction of the unsaturated diamine there are slurried (at 76, FIG. 1) 30 grams/hour of 5% Pd on $Al_2O_3$.

The suspension is sent into an autoclave (78, FIG. 1), heated to 100° C at a hydrogen pressure of 80 Atmospheres. After 3 hours and 30 minutes of reaction, the suspension issuing from the autoclave is filtered under heating to recover the catalyst (80, FIG. 1) and treated at 90° C with $CO_2$ (82, FIG. 1). By cooling, the saturated aminoacid crystallizes (86, FIG. 1), and is separated by filtration (88, FIG. 1). It consists of 403 grams/hour of product, m.p. 180°–182° C.

The mother liquors are acidified, pH 2, obtaining a precipitate of 21 grams/hour consisting of impure decandicarboxylic acid, the impurities being nitrogenous by-products.

EXAMPLE IV-1-Bis PREPARATION OF 8-AMINO-OCTANOIC ACID FROM 8-AMINO OCTENOIC ACID

Operation is carried out as described in the Example IV-1, effecting the hydrogenation of the double bond of the barium salt of the 8-amino octenoic acid. In this case, the separation of the saturated aminoacid is effected by precipitating the barium as sulphate, filtering and bringing the aqueous solution of the aminoacid to dryness. By crystallization using propyl alcohol/$H_2O$, there is obtained the 8-aminooctanoic acid, m.p. 190°–191° C.

EXAMPLE IV-1-Tris — Preparation of 10-AMINO-DECANOIC ACID FROM THE 10-AMINO-DECENOIC ACIDS Operation is carried out as described in the Example No. IV-1 effecting the hydrogenation of the double bond of the 10-aminodecenoic acids. By performing the separation as described in the Example IV-1-Bis, there is obtained the 10-amino-decanoic acid, m.p. 185°–186° C.

IV-2 PREPARATION OF THE 12-AMINO-DODECANOIC ACID FROM THE UNSATURATED AMINOACID AS OBTAINED BY REDUCTIVE AMINATION OF THE TRANSPOSITION PRODUCTS OF THE MONO-OZONIDE OF MIXTURES OF CDT ISOMERS

The saturated amino acid is prepared from stereoisomeric mixtures of unsaturated aminoacids. The procedure is as in IV-1 by employing the product obtained in III-3. There are obtained 408 grams/hour of 12-aminododecanoic acid, m.p. 179° C–182° C.

IV-3 PREPARATION OF THE 12-AMINODODECANOIC ACID AND OF THE 12-AMINO-t,t-4,8-DODECADIENOIC ACID.

A modification is carried out of the method of preparation of the saturated amino acid, by separating that fraction of unsaturated amino acid which is obtained by treatment with $CO_2$ at 0° C of the alkaline solutions of the unsaturated amino acid.

Example III-1 is repeated. Upon extraction of the unsaturated diamine, the solution of the sodium salt of the 12-amino-t,t-4,8-dodecadienoic acid is treated at 0° C with $CO_2$. There are obtained by crystallization 245 grams/hour of unsaturated aminoacid, m.p. 188° C–190° C. The remaining solution is hydrogenated as in Example IV-1 and 162 grams/hour of saturated aminoacid are thus obtained, m.p. 180° C–182° C.

IV-4 PREPARATION OF DODECAMETHYLENEDIAMINE AND 12-AMINODODECANOIC ACID

This example describes the preparation of the saturated diamine and the saturated amino acid. The procedure is the same as in Example III-1. The solution of the sodium salt of the 12-amino-t,t-4,8-dodecadienoic acid and of 1,12-diaminododecadiene-(4,8) is supplemented with the palladium catalyst and hydrogenated as in Example IV-1. The hydrogenated product is extracted with toluene and treated with $CO_2$ as in Example III-1 while the residual solution is treated with $CO_2$ as in Example IV-1. There are obtained 15.1 grams/hour of dodecamethylenediamine carbamate and 401 grams/hour of 12-aminododecanoic acid.

IV-5 PREPARATION OF 12-AMINODODECANOIC ACID

The saturated aminoacid is prepared from the unsaturated aminoacid purified and dissolved in an organic solvent. A 100 gram sample of 12-amino-t,t-4,8-dodecadienoic acid is dissolved in 900 grams of a solution of water/n-propanol (1 : 1). 5 grams of palladium on alumina are added and hydrogenated for 2 hours at 100° C–30 Atm. After filtration of the catalyst by cooling, crystallization takes place of 91 grams of 12-aminododecanoic acid, m.p. 181°–183° C.

IV-6 POLYCONDENSATION OF 12-AMINODODECANOIC ACID 20 grams of saturated aminoac-id is polycondensed as described in the Example III-5.

There is obtained 18.1 grams of polymer having intrinsic viscosity of 1.28 in m-cresol.

IV-6-bis POLYCONDENSATION OF 8-AMINO-OCTANOIC ACID 10 grams of 8-amino-octanoic acid are polycondensed as described in the Example III-5.

There is obtained 9.1 grams of polymer having intrinsic viscosity of 1,2 in m-cresol.

EXAMPLES: GROUP V (UNSATURATED DERIVATIVES OF THE ACIDIC ALDEHYDE)

V-1 PREPARATION OF THE 12-HYDROXYDODECAN-t,t-4,8-DIENOIC ACID

Certain derivatives of the transposition product of the CDT ozonide, of interest in themselves and serving, in addition, to establish the purity of the obtained acidic aldehyde, are prepared in the examples that follow.

50 grams of the unsaturated acidic aldehyde prepared according to the Example II-1 (b.p. at 3 mm Hg = 180°–183° C) are charged into a 1-liter glass flask and then, under stirring, addition is made of 250 cc of ethyl alcohol; then cooling is effected to 0° C and addition is made of 19.2 grams of sodium bicarbonate dissolved in 250 ml of water. On completion of the addition of the sodium bicarbonate solution, the apparatus is placed under vacuum and the temperature is taken to 20°–25° C.

While all the carbon dioxide has evolved, cooling is again effected to 0° C and slow addition is made of 7 grams of sodium borhydride dissolved in 60 ml water. The solution is allowed to stand for 1 hour at 0° C and overnight at room temperature; then evaporation is carried out to small volume under vacuum in a stream of $CO_2$ in order to decompose the majority of the excess of sodium borhydride.

Then 50 ml of N/1 NaOH are added and extracted with ether; the ether extract is evaporated to dryness. In this way there is obtained a residue (2.2 grams) consisting of a mixture of cyclododecatriene and dodecadien-(4,8)-dio-(1,12).

The aqueous phase, acidified with hydrochloric acid to pH 2, is again extracted with ether and the extract is washed with 30 ml water, dried over magnesium sulfate and evaporated to dryness. The residue consists of 39.5 grams of 12-hydroxydodecane-t,t-4,8-dienoic acid, as results from the following analytical data:

|  | Calculated millimols/gram | Found millimols/gram |
| --- | --- | --- |
| Hydroxyl group | 4.72 | 4.60 |
| Acidic groups | 4.72 | 4.68 |
| Double bonds | 9.44 | 9.20 |

V-1-bis PREPARATION OF 8-HYDROXY-CIS-4-OCTENOIC ACID

Operation is carried out as described in the Example V-1, using the 7-formyl-cis-4-heptenoic acid, obtaining after reduction with $NaBH_4$ the 8-hydroxy-cis-4-octenoic acid.

V-2 PREPARATION OF THE METHYL ESTER OF THE 12-HYDROXYDODECANE-t,t-4,8-DIENOIC ACID 20 grams of hydroxy acid obtained in the Examples V-1 are dissolved in ether and treated with an ethereal solution of diazomethane. By evaporation of the solvent there is obtained 21.5 grams of the methyl ester of the 12-hydroxydodecane-t,t-4,8-dienoic acid.

V-3 PREPARATION OF 1,12-DODECANEDIOL

Dodecandien-(4,8)-diol-(1,12) (2 grams) is subjected to reduction in ethanol, using Pd on carbon as catalyst.

There is obtained, after filtration of the catalyst and evaporation of the solvent, 2.04 grams of 1,12-dodecanediol.

What is claimed is:

1. A method for the production of aldehyde acids and their unsaturated derivatives from cycloolefins, comprising
    subjecting a solution containing a cyclo-olefin in a concentration of from about 10 to 40% by weight, and having more than one unsaturation, to a selective ozonization step in the presence of a solvent mixture of at least one non-polar solvent and at least one polar solvent, whereby the mono-ozonide of the said cyclo-olefin is obtained, and
    subjecting said mono-ozonide to at least one transposition step, to obtain an omega-formyl-alkenoic acid,
    said mono-ozonide, as soon as it forms, reacting with said polar solvent to produce a heavy phase which is insoluble in said solution, and which separates therefrom during said ozonization step, whereby not more than one olefinic unsaturation is removed by said ozonization step, and
    said solvent mixture further including an organic acid anhydride, with the weight ratio of said anhydride to the polar solvent being set at between 1:2 and 2:1.

2. A method according to claim 1, wherein said non-polar solvent is a saturated hydrocarbon.

3. A method according to claim 2, characterized by the fact that the said selective ozonization is effected in a reactor, and including
decanting the heavy phase containing the mono-ozonide from the reactor, and
recycling at least part of the residue from said transposition step to the reactor.

4. A method according to claim 2, characterized by the fact that the said solvent mixture contains from 60 to 98% by weight of saturated hydrocarbons and from 2 to 40% of polar solvents.

5. A method according to claim 2, characterized in that the said solvent mixture comprises aliphatic and cycloaliphatic hydrocarbons.

6. A method according to claim 5, characterized in that the aliphatic hydrocarbon is cyclohexane.

7. A method according to claim 5, characterized in that the aliphatic hydrocarbon in paraffin oil.

8. A method according to claim 2, characterized in that the polar solvent is an aliphatic carboxylic acid.

9. A method according to claim 8, characterized in that the said aliphatic carboxylic acid comprises acetic acid.

10. A method according to claim 9, characterized in that the said polar solvent consists of a mixture of acetic acid and acetic anhydride.

11. A method according to claim 2, characterized in that the said selective ozonization is performed at a temperature between 5° C and 50° C.

12. A method according to claim 2, characterized in that the said selective ozonization is performed using as ozonizing means a mixture of ozone, oxygen and carbon dioxide, containing from 2 to 60 g. of ozone per cubic meter.

13. A method according to claim 2, characterized in that the said selective ozonization is performed using as ozonizing means a mixture of ozone and air containing from 1 to 50 grams of ozone per cubic meter.

14. A method according to claim 13, characterized in that said mixture of ozone and air is free from oxides of nitrogen.

15. A method according to claim 14, characterized in that said mixture of ozone and air is purified of the oxides of nitrogen by means of prior passing into a solution of sodium or potassium acetate of from 1 to 10% in acetic acid.

16. A method according to claim 14, characterized in that said mixture of ozone and air is purified of nitrogen oxides by means of prior passing over copper oxide chips.

17. A method according to claim 1, characterized in that
the polyunsaturated cyclo-olefin is selectively ozonized by means of treatment with ozone diluted to an extent of from 2 to 6 grams per 100 liters of a gas chosen from the group consisting of air, oxygen, carbon dioxide and mixtures thereof, and fed into the presence of said solution in the form of a gaseous stream at the approximate rate of 1 mole of ozone for every 1–1.2 moles of cyclo-olefin, which olefin comes into contact with the ozone in a first area
said solution including from 55% to 85% by weight of a non-polar solvent consisting of a saturated aliphatic hydrocarbon or of several saturated aliphatic hydrocarbons, and from 5 to 10% of polar solvents including acetic acid and acetic anhydride,
said heavier phase including an unsaturated peroxide derivative of a mono-ozonide, and
said peroxide derivative thereafter being subjected to successive steps of transposition and of hydrolysis to obtain said omego-formyl-alkenoic acid.

18. A method according to claim 17, characterized in that the said steps of transposition and hydrolysis comprise the treatment in inert gas atmosphere of the said unsaturated peroxide derivative in a solvent mixture consisting of acetic anhydride in peroxide derivative-/anhydride molar ratio of from: 1:1 to 1:7, acetic acid in peroxide derivative/acetic acid molar ratio of from 1:1 to 1:7, and with the sodium acetate, the potassium acetate and the pyridine acetate in quantities of acetate from 0.025 to 0.1 moles per mole of peroxide derivative, at temperatures not greater than 45° C, thereby obtaining omegaformylalkenoic acid together with quantities of the relative anhydride.

19. A method according to claim 2, characterized in that the heavy phase containing monoozonide of the polyunsaturated cyclo-olefin, the polar solvents and quantities lower than 20% by weight of non-ozonized olefin and of saturated hydrocarbons, is subjected to catalytic transposition with formation of a mixture of acidic aldehyde and of the corresponding aldehydic anhydrides, and said mixture of acidic aldehyde and aldehyde and anhydrides is transformed into an omega-formyl-alkenoic acid by means of hydrolysis at temperatures of from 30° C to 100° C, in the presence of 0.2–20 moles of water per mole of acidic aldehyde.

20. A method according to claim 1, characterized in that the said cyclo-olefin consists of an unsaturated cyclo-olefin selected from the group consisting of 1,5,9-cyclodecatriene (in all of its forms or a mixture of the stereoisomeric forms) of 1,5-cyclo-octadiene and 1,5-cyclodecadiene, and the omegaformyl-alkenoic acid is selected from the group consisting of 11-formyl-4,8-undecadienoic acid, 7-formyl-4-heptenoic acid and 9-formyl-4-nonenoic acid and 9-formyl-6-nonenoic acid.

21. A method according to claim 20, characterized in that the omega-formyl-alkenoic acid is subjected to a process of selective reduction on the formyl group, obtaining the corresponding omega-hydroxy-alkenoic acid.

22. A method according to claim 21, characterized in that the omega-hydroxy-alkenoic acid is subjected to a process of esterification, obtaining an unsaturated ester.

* * * * *

UNITED STATES PATENT OFFICE
CERTIFICATE OF CORRECTION

Patent No. 4,085,127            Dated April 18, 1978

Inventor(s) Francesco Siclari and Paolo Rossi

It is certified that error appears in the above-identified patent and that said Letters Patent are hereby corrected as shown below:

On the title page, in paragraph [73], line 2,
"Application" should read -- Applicazioni --.

Signed and Sealed this

Tenth Day of October 1978

[SEAL]

Attest:

RUTH C. MASON
*Attesting Officer*

DONALD W. BANNER
*Commissioner of Patents and Trademarks*